(12) United States Patent
Psarrakis et al.

(10) Patent No.: US 11,096,915 B2
(45) Date of Patent: Aug. 24, 2021

(54) METHODS FOR THE PREPARATION OF A LEVOTHYROXINE SOLUTION

(71) Applicant: EMP Levo US B.V., Amsterdam (NL)

(72) Inventors: Yannis Psarrakis, Lavrion-Attica (GR); Konstantinos Lioumis, Lavrion-Attica (GR)

(73) Assignee: EMP Levo US B.V., Amsterdam (NL)

( * ) Notice: Subject to any disclaimer, the term of this patent is extended or adjusted under 35 U.S.C. 154(b) by 0 days.

(21) Appl. No.: 16/315,549

(22) PCT Filed: Jul. 5, 2017

(86) PCT No.: PCT/EP2017/066823
§ 371 (c)(1),
(2) Date: Jan. 4, 2019

(87) PCT Pub. No.: WO2018/007466
PCT Pub. Date: Jan. 11, 2018

(65) Prior Publication Data
US 2019/0321316 A1    Oct. 24, 2019

Related U.S. Application Data

(60) Provisional application No. 62/358,270, filed on May 5, 2016.

(30) Foreign Application Priority Data

Jul. 5, 2016 (NL) .................................... 2017110

(51) Int. Cl.
*A61K 31/198* (2006.01)
*A61K 9/00* (2006.01)
*A61K 47/02* (2006.01)
*A61K 47/10* (2017.01)
*A61K 47/12* (2006.01)
*A61K 47/14* (2017.01)
*A61K 47/26* (2006.01)

(52) U.S. Cl.
CPC .......... *A61K 31/198* (2013.01); *A61K 9/0053* (2013.01); *A61K 47/02* (2013.01); *A61K 47/10* (2013.01); *A61K 47/12* (2013.01); *A61K 47/14* (2013.01); *A61K 47/26* (2013.01)

(58) Field of Classification Search
CPC ................................................ A61K 31/055
See application file for complete search history.

(56) References Cited

U.S. PATENT DOCUMENTS

| 8,779,000 B1 * | 7/2014 | Parikh ................. A61K 31/195 514/567 |
| 9,050,307 B2 * | 6/2015 | Psarrakis ............. A61K 31/198 |
| 9,345,772 B1 | 5/2016 | Parikh et al. |
| 2003/0198668 A1 | 10/2003 | Franz et al. |
| 2003/0199588 A1 | 10/2003 | Franz et al. |

FOREIGN PATENT DOCUMENTS

| EP | 2692340 A1 | 2/2014 | |
| GB | 2191695 A | 12/1987 | |
| WO | 2007/077252 A1 | 7/2007 | |
| WO | WO-2009136249 A1 * | 11/2009 | ........... C07C 229/36 |
| WO | 2012/120338 A1 | 9/2012 | |
| WO | WO-2012120338 A1 * | 9/2012 | ........... A61K 31/198 |
| WO | WO2012120338 A1 * | 9/2012 | ........... A61K 31/055 |
| WO | 2015/151013 A1 | 10/2015 | |

OTHER PUBLICATIONS

Patel, H., International Journal of Pharmaceutics vol. 264 pp. 35-43. Published 2003. (Year: 2003).*
Boulton et al., Stability of an extemporaneously compounded levothyroxine sodium oral liquid, American Society of Health-System Pharmacists, 1157-1161 (1996).

* cited by examiner

*Primary Examiner* — Theodore R. Howell
*Assistant Examiner* — George W Kosturko
(74) *Attorney, Agent, or Firm* — Browdy and Neimark, PLLC

(57) ABSTRACT

Described is a method for the preparation of an oral levothyroxine composition, comprising the steps of combining levothyroxine or a salt thereof, a water-miscible organic solvent or a sugar alcohol and water, adjusting the pH to at least 8 providing a basic aqueous medium, dissolving the levothyroxine in the basic aqueous medium to yield a levothyroxine solution, and lowering the pH of the levothyroxine solution to between 3.5-4.9. also described is an oral levothyroxine composition obtainable by the said method and its use as a medicament.

18 Claims, No Drawings

METHODS FOR THE PREPARATION OF A LEVOTHYROXINE SOLUTION

FIELD OF THE INVENTION

The invention relates to a method for the preparation of a levothyroxine solution and to a solution thereof.

BACKGROUND OF THE INVENTION

Levothyroxine, also known as L-thyroxine, synthetic T4, or 3,5,3',5'-tetraiodo-L-thyronine, CAS number 51-48-9, is a synthetic form of thyroxine, used as a hormone substitute for patients with thyroid conditions, such as hypothyroidism, as well as conditions in which the thyroid gland becomes enlarged, causing swelling of the neck. The structural formula of the levothyroxine acid, is

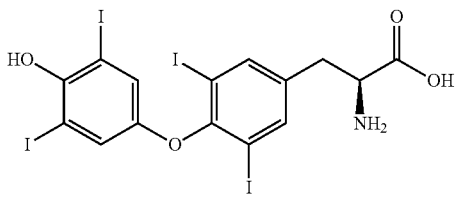 [SMILES: N[C@@H](Cc1cc(I)c(Oc2cc(I)c(O)c(I)c2)c(I)c1)C(=O)O]

Thyroid hormones regulate multiple metabolic processes and play an essential role in normal growth and development, and normal maturation of the central nervous system and bone. The levothyroxine salt levothyroxine sodium was initially manufactured as synthetic T4 in 1958 and was introduced on the market as before 1962.

Levothyroxine salts, like the sodium salt are very slightly soluble in water and slightly soluble in 96% ethanol. Levothyroxine sodium is described in the European Pharmacopoeia. The chemical designation of levothyroxine sodium is sodium (2S)-2-amino-3-[4-(4-hydroxy-3,5-diiodophenoxy)-3,5-diiodophenyl]-propanoate. Its molecular formula is $C_{15}H_{10}I_4NNaO_4$, $xH_2O$ and its molecular weight is 799 (anhydrous substance). The structural formula of levothyroxine sodium is:

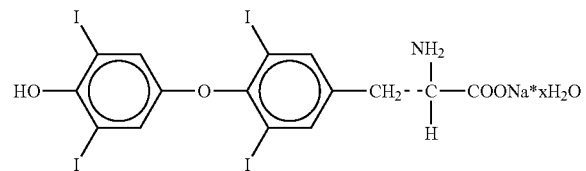

Orally administered levothyroxine sodium is used as replacement therapy in conditions characterized by diminished or absent thyroid function such as cretinism, myxedema, non-toxic goitre, thyroid carcinoma and hypothyroidism (Food and Drug Administration 1997; Wertheimer and Santella 2005).

Solid formulations (tablets, softgel capsules) and liquid formulations for oral use are known. The big advantage of the solution is the uniformity of dosage units in comparison to solid dosage forms (tablets). The tablets, usually due to the very low levothyroxine content (0.04% up to 0.5% w/w), have problems of content uniformity during the production process and many times the actual content that the patient receives with tablet therapy, is not 100% but could range from 85% up to 120% and this creates serious problems on patient treatment.

Oral solutions of levothyroxine are particularly suitable for use in children and in the elderly who may have difficulty to swallow tablets. Unfortunately, solutions of levothyroxine are less stable compared to tablets during storage. Also, levothyroxine solutions may comprise relatively high amounts of liothyronine, which is believed to be the source of side-effects in certain patients. Aqueous levothyroxine solutions are however prone to decomposition compared to the solid forms, and to and particle formation. Indeed, the product Evotrox (Kappin, UK) was removed from the UK market in 2012 because of variable stability, as a result of which the product quality could not be assured.

GB2191695 describes the fact that levothyroxine dissolves in an aqueous solution at pH 11-12, but turns into a white pale suspension when the pH is lowered to pH 7. Lowering the pH further to pH 5-6 results in the formation of a precipitate.

An improved oral levothyroxine solution is described in WO2012/120338, wherein the sodium salt of levothyroxine was dissolved in an aqueous medium comprising glycerol at basic pH, whereafter the pH was lowered to 5-6. The obtained preparation was still a clear solution. As compared to Evotrox, significantly less liothyronine and other impurities were formed after storage for 2 to 6 months both at ambient temperature as well as at 40° C.

Nevertheless, for stability reasons, the oral levothyroxine solution of WO2012/120338 still needs refrigeration during storage and transport.

U.S. Pat. No. 9,345,772 describes an pharmaceutical composition comprising levothyroxine, glycerol, EDTA and water. It is described that the presence of EDTA make the pH shift as described in WO2012/120338 superfluous and that a stable solution is obtained. However, the stability is only tested for a duration of three days at 70° C., which is not in conformity with the conditions of the International Council for Harmonisation of Technical Requirements for Pharmaceuticals for Human Use (ICH), where e.g. a 6 months storage at 40° C. is prescribed, see ICH Guideline "Stability Testing of New Drug Substances and Products/' Q1A(R2) of Feb. 6, 2003, table 2.1.7.1. The present inventors have observed that the stability of the Levothyroxine solutions 1 and 2 of U.S. Pat. No. 9,345,772 is independent on the presence of EDTA. A technical effect for EDTA could therefore not be observed. Further, the levothyroxine solution of U.S. Pat. No. 9,345,772 loses significant stability after 1 month at 40° C. In addition thereto, the solutions of U.S. Pat. No. 9,345,772 are prone to microbial decay.

Herein, an oral levothyroxine solution is disclosed wherein the stability is even more improved, in particular when stored for 6 months at elevated temperatures of up to 40° C., indicating that for the first time, an oral levothyroxine solution is provided that does not need refrigeration during preparation, transport and storage.

Accordingly, provided is a method for the preparation of an oral levothyroxine composition, comprising steps of:
  a) combining:
    i. levothyroxine or a salt thereof,
    ii. a water-miscible organic solvent or a sugar alcohol or a combination thereof,
    iii. water,
  b) adjusting the pH to at least 8 providing a basic aqueous medium,
  c) dissolving the levothyroxine in the basic aqueous medium to yield a levothyroxine solution, and d) lowering the pH of the levothyroxine solution to between 3.5-4.9.

It has surprisingly been found that levothyroxine, when dissolved in an aqueous basic medium comprising a water soluble organic solvent, remains stable in solution when, after dissolution, the pH is lowered to below 5, e.g. to between 3.5-4.9, even at 40° C. for 6 months. It has been found that at such conditions, conversion of the initial levothyroxine to liothyronine is reduced to about two-third as compared to the conversion when the pH is lowered to only 5.5, when the remaining conditions are identical.

When the term "organic solvent" is used herein, it is to be understood that the same would be applicable for an aqueous solution of sugar alcohol, in particular wherein such a solution would comprise a similar weight of sugar alcohol as compared to the weight of the solvent, preferably having a volume as close to that of the solvent. For example, 3 ml of glycerol (weighing 3.78 g) would be comparable with an aqueous solution comprising the same weight of sugar alcohol, and preferably in a volume of 3 ml or as close as possible to said volume. It is also to be understood that any combination of sugar alcohol and water miscible solvent can replace the sugar alcohol or the said water miscible solvent.

The levothyroxine or salt thereof is combined with a water-miscible organic solvent or a sugar alcohol or a combination thereof and with water. The pH is adjusted to a basic value of at least 8. The order of combining the above ingredients can be chosen as desired. For example, the levothyroxine can be mixed with water-miscible organic solvent, whereafter water is added, or the levothyroxine can be mixed with water whereafter the organic solvent can be added. If instead of the solvent a sugar alcohol is used, the said sugar alcohol can be dissolved in water before being combined.

Accordingly, it is also possible that a portion of the water and a portion of the water miscible organic solvent or sugar alcohol are combined and mixed with the levothyroxine or salt thereof to prepare a premix, whereafter the remaining water and solvent are added. The levothyroxine or salt thereof can also be mixed with a portion of the miscible organic solvent and water, followed by addition of the remaining portion of the solvent. Alternatively, the levothyroxine can be mixed with all the solvent and the water. It is also possible to bring the pH of the water to an envisaged basic value, and to add the said water to a mixture of levothyroxine in water miscible organic solvent, optionally already combined with a portion of the water. In a preferred embodiment, the levothyroxine or salt thereof is mixed with a portion of the water miscible organic solvent, optionally combined with a portion of the water, which portion is preferably less (in volume) than the organic solvent, resulting in a premix, whereafter the remaining solvent (or sugar alcohol) and water are added, the water preferably being brought to an envisaged basic pH so that addition of the said remaining water also results in the envisaged pH adjustment. The premix preferably is 10 to 100 times as concentrated with respect of the levothyroxine concentration as compared to the final composition.

However, the pH can also be adjusted after the envisaged volumes of water miscible organic solvent and water are mixed with the levothyroxine or salt thereof. After the above step of combining the levothyroxine with the water miscible organic solvent or the sugar alcohol and the water and pH adjustment to at least 8, a basic aqueous medium is provided comprising the levothyroxine provided in step a). The term 'aqueous' in this respect does not necessarily mean that the volume of the water in the medium is more than the volume of the solvent. It merely means that the medium comprises water, e.g. as added in the combination step. Although dissolution of the levothyroxine or salt thereof can already start in the combination step a), with the water miscible organic solvent or with the water or an aqueous solution of the sugar alcohol, or a combination thereof, dissolution of the levothyroxine takes at least place upon pH adjustment to the envisaged basic value of at least 8, i.e. during and after step b), said dissolution preferably being complete, to yield a levothyroxine solution. After pH adjustment and dissolution of the levothyroxine, the pH of the levothyroxine solution is lowered to between 3.5 and 4.8.

The skilled person is aware of suitable water miscible organic solvents. In particular, such solvents are liquid at ambient pressure and temperature, at least when combined with the envisaged volume of water, and in particular in the temperature range of 20-50° C., more preferably the temperature range is broader, i.e. over 15-60° C. or broader. The term 'miscible' means that the solvent mixes with water into a single phase, at least at the pH of the envisaged oral solution, i.e. of 3.5-4.8. In particular, the levothyroxine or salt thereof is capable of at least partially dissolving in the said solvent or the aqueous solution of sugar alcohol, in order to expedite the dissolution process. However, this is not necessary as long as adjusting the pH as described above to an envisaged basic value of at least 8 results in dissolution of the levothyroxine or salt thereof.

Although levothyroxine can be provided in its native acid form, it is preferred to provide the levothyroxine as a salt, preferably as an alkali or earth alkali salt, such as potassium, calcium and sodium salt, most preferably as sodium salt. The said salts are better soluble resulting in a more effective dissolution process. Processes for the preparation of sodium salt of levothyroxine have been described among others in J. Chem. Soc, (1949): 3424-3, IT1302201, WO2015/151013, U.S. Pat. No. 5,917,087, WO2009/136245. The provided levothyroxine salt and optional other ingredients are preferably all of pharmaceutical quality.

The levothyroxine is mixed with a water miscible organic solvent, preferably resulting in a dispersion. Mixing may be performed while being agitated during any suitable time period, readily determined by the skilled person, e.g. during 5 to 60 minutes, or 10 to 40 minutes or 15 to 30 minutes.

Preferably, the water miscible organic solvent is a compound selected from the group consisting of: polyols, such as alkane triols and glycols, such as alkane diols and polyethylene glycol; alcohols, such as ethanol, isopropyl alcohol, benzyl alcohol; acetone, benzyl benzoate, phthalates, such as dibutyl phthalate, diethyl phthalate, dimethyl phthalate; dimethyl sulfoxide, dimethylacetamide, glycofurol, isopropyl myristate, isopropyl palmitate, propylene carbonate, pyrrolidine, glycerine triacetate, triethyl citrate, triolein, or a combination of two or more thereof. Again, the skilled person immediately understands that such solvents should be liquid and miscible with water, at least in the temperature and pH ranges as indicated above.

In an embodiment, the water-miscible organic solvent in step a) comprises a polyol, chosen from the group, consisting of $C_3$-$C_5$ alkane diols and alkane triols or a combination of two or more thereof. In another embodiment, the water-miscible organic solvent is chosen from the group, consisting of glycerol, propylene glycol (i.e. 1,2-propanediol), 1,3-propanediol, butylene glycol and ethylene glycol or a combination of two or more thereof. In a particular embodiment, the polyol comprises propylene glycol or glycerol, in particular glycerol. It was found that the most stable oral solutions were obtained when propylene glycol and in particular glycerol were used as water miscible organic solvent.

In particular, the sugar alcohol is chosen from the group, consisting of maltitol, sorbitol and maltodextrin. However, the skilled person will be capable of choosing alternatively suitable sugar alcohols, as long as these remain in solution in the envisaged composition. For this reason, mannitol and xylitol appear to be less suitable as these sugar alcohols seem to precipitate at the envisaged pH of 3.5-4.8.

In an embodiment, after steps b) and c), i.e. after the levothyroxine is combined with both the water miscible organic solvent or sugar alcohol and the water, the ratio between the water and the water miscible organic solvent or the sugar alcohol is in the range of 1:0.1-20 (i.e. 10:1 to 1:20), 1:0.1-10 (i.e. 10:1 to 1:10), 1:0.25-10 (i.e. 4:1 to 1:10), 1:0.25-4 (i.e. 4:1 to 1:4), 1:1-3, (i.e. 1:1 to 1:3) or 1:1.5-2.5 (i.e. 2:3 to 2:5).

In another embodiment, the composition comprises 20-80 w/w %, 35-75 w/w %, or 50-75 w/w % water miscible solvent or sugar alcohol based on the total weight of the composition. Such amounts provide a stable levothyroxine solution at the envisaged pH. The final concentration of the sugar alcohol is usually between 1M and 5M, preferably about 1.5-4M.

In step b) the pH is adjusted to at least 8 preferably to between 9 and 11, preferably to about 10. The term 'about' here allows a deviation of 0.2 from 10, i.e. a range of 9.8 to 10.2. The pH is preferably determined and monitored, e.g. by using a calibrated electronic pH meter based on electrode potential. Preferably, adjusting the pH in step d) comprises adding a base. Preferably, the pH should be adjusted by adding small amount of base to the mixture while mixing or stirring, and allowing to homogenize and stabilize the measured pH before proceeding to further adjust the pH. The base may be in the form of pellets, flakes, granules, or an aqueous solution at an envisaged concentration or a number of different concentrations. Preferably, the base is added as an aqueous solution, for instance with a concentration in the order of 0.1-2 mol/l. Suitable bases comprise potassium bicarbonate, potassium citrate, potassium citrate, potassium hydroxide, sodium carbonate, calcium hydroxide, ammonia Solution, sodium hydroxide, sodium borate, monoethanolamine, sodium citrate dihydrate, diethanolamine, triethanolamine and sodium bicarbonate. Preferably, the added base comprises sodium hydroxide, in particular as a solution. Adding sodium hydroxide is pharmaceutically acceptable and yields a stable solution.

Lowering of the pH of the levothyroxine solution in step d) to below 5, i.e. below 4.9 or 4.8, in particular between 3.5-4.8 results in a very attractive oral levothyroxine solution which is stable during storage for 6 months at 40° C. or even longer. Such a solution is very suitable for administering to a patient.

Preferably, lowering the pH of the levothyroxine solution in step d) comprises adding a carboxylic acid. Carboxylic acids, preferably water-soluble carboxylic acids, showed a good stability. Suitable carboxylic acids comprise lauric acid, tartaric acid, acetic acid, glacial, maleic acid and sorbic acid. In a particular embodiment, the carboxylic acid comprises citric acid, which is well tolerated, compatible with levothyroxine and gave good results.

In a particular embodiment, the method further comprises the step of buffering the composition, the buffer comprising an acidic buffer component and a basic buffer component. Buffering will result in a more stable maintenance of the pH over time during storage of the solution. The skilled person is well aware of suitable buffers for the envisaged pH range of 3.5-4.9 or a smaller range therein. As the solution is for oral use, the buffer should preferably be acceptable for this purpose. As the described method comprises a step of elevating the pH, the basic buffer component is preferably added in step a) or b). As the described method comprises a step of lowering the pH, the acidic buffer component is preferably added in step d).

Suitabe buffers are e.g. citric acid-sodium or potassium citrate, in particular citric acid-sodium citrate, boric acid-sodium borate, hydrochloric acid-potassium hydrogen phthalate, adipic acid-sodium adipate, acetic acid-sodium acetate, potassium hydrogen phthalate-sodium hydroxide, malic acid-sodium malate, maleic acid-sodium maleate.

Preferably in step d), the pH is lowered to between 3.5 and 4.8, more preferably 3.8-4.5, in particular to 3.8-4.2, resulting in the most stable solutions, i.e. comprising, after 6 months storage at 40° C., up to 94% or even more of the levothyroxine added in step a).

Although not deemed necessary, heating may be performed during step a), b) and/or c) to expedite the dissolution process. For example once mixed with the water miscible organic solvent and optionally a (portion of) the water, or with an aqueous solution of the sugar alcohol, said mixture can be heated to 40-50° C. for e.g. 5 to 60 minutes or 15 to 30 minutes, but heating has been found to possibly have a negative effect on the stability of the envisaged oral solution. For that reason, it may be preferred to mix the levothyroxine with the solvent without heating, and to perform each of steps a)-d) at ambient temperature, i.e. between 18 and 25° C. Accordingly, addition of water is preferably performed at ambient temperature, with water of ambient temperature, although indeed the water can be preheated, however again with the possible result that the oral solution becomes less stable. Preferably, the components, including liquids, that are added during steps a)-d) are at ambient temperature.

As levothyroxine may show degradation under the influence of UV and blue light, the process is preferably performed in the dark or in dark glass comprising a UV-filter.

In an attractive embodiment, the method comprises a further step e) comprising the addition of a preservative and allowing the preservative to dissolve. Step e) can be performed during or after any of the steps of the method. Preferably, the preservative is added before step d). The addition and dissolution of a preservative results in an even more increased stability. Step e) is preferably preformed at ambient temperature for the reasons explained above.

Preferred preservatives comprise benzoic acid, sorbic acid, propylene glycol and paraben or a salt thereof or a combination of two or more thereof. At the low pH of 3.5-4.9 it was shown that in particular sodium benzoate, potassium benzoate, sodium sorbate and potassium sorbate are suitable preservatives, as well as benzoic acid and sorbic acid. The benzoate and sorbate salts are readily dissolvable at ambient temperature, and from this point of view, the benzoate and sorbate salts are preferred over the respective acids. Benzoic acid is preferably present in the solution in the range of 0.01 to 0.2 v/w %, sodium or potassium benzoate in the range of 0.02 to 0.5 w/v %, sorbic acid in the range of 0.05 to 0.2 w/v %, sodium sorbate and potassium sorbate in the range of 0.1 to 0.2 w/v %. Other suitable preservatives comprise bronopol, imidurea, phenoxyethanol, phenylmercuric acetate, benzyl alcohol, phenylmercuric borate, chlorocresol, benzethonium chloride, phenylethyl alcohol, benzalkonium chloride, hexetidine, chlorobutanol, cresol, cetylpyridinium chloride, phenylmercuric nitrate, chloroxylenol, propionic acid, phenol, thimerosal, sulfur dioxide, boric acid, edetic acid, sodium propionate, calcium chloride, sodium acetate, sodium sulfite, monothioglycerol, cetrimide, calcium acetate, butylene glycol, sodium metabisulfite, alcohol, propyl gallate, potassium metabisulfite, sodium lactate, chlorhexidine, calcium lactate, pentetic acid, propylene glycol alginate, sodium borate, magnesium trisilicate, isopropyl alcohol, dimethyl ether, butylated hydroxyanisole, pyrrolidone, lactic acid, sodium lauryl sulphate and dimethyl sulfoxide.

In an attractive embodiment, the preservative comprises one or more parabens, chosen from the group consisting of methylparaben, ethylparaben, propylparaben, butylparaben, salts thereof, in particular alkali salts such as sodium salts, or a combination of two or more thereof. Sodium methylparaben is also known as sodium methyl parahydroxybenzoate, and sodium propylparaben also known as sodium propyl parahydroxybenzoate. In particular, the preservative comprises sodium methylparaben, sodium propylparaben or a combination thereof which showed a good compatibility with levothyroxine. However, benzoic acid and sorbic acid as well as the salts thereof as described above have shown to have improved preservative activity at low pH.

In another attractive embodiment, the method comprises a further step f) comprising the addition of an additive, such as a sweetening agent, colouring agent or any additive known to the skilled person to be suitable in the present composition. Preferably, the additive is added before step d).

Also provided is an oral levothyroxine solution obtainable by the described method. Said oral levothyroxine solution preferably comprises, after storage at 40° C. for at least 6 months, at least 93%, preferably at least 94% or at least 95% or even at least 96% of the levothyroxine as provided in step a).

In an attractive embodiment, the oral levothyroxine solution comprises levothyroxine or a salt thereof at a concentration of 2-30 µg/ml of the composition. In particular, the oral solution comprises a sodium levothyroxine concentration of approximately 25 µg in 5 ml, approximately 50 µg in 5 ml or approximately 100 µg in 5 ml, wherein the composition further comprises a water miscible organic solvent or a sugar alcohol, or a combination thereof, and water, having a pH of 3.5-4.8. preferably of 3.5-4.5 or 3.8-4.2. Preferably the water miscible organic solvent in the composition of the invention comprises propylene glycol, glycerol or a combination thereof. More preferably the water miscible organic solvent comprises glycerol. The sugar alcohol in the levothyroxine solution preferably comprises maltitol, maltodextrin or sorbitol or a combination thereof, preferably maltitol.

In an attractive embodiment, the oral solution further comprises a preservative, in particular chosen from the group, consisting of benzoic acid, sorbic acid, propylene glycol and parabens, or salts thereof or a combination of two or more thereof. As indicated above, in an attractive embodiment, the preservative comprises sodium benzoate or potassium benzoate. In case of a paraben as preservative, it can be chosen from e.g. methylparaben, such as sodium methylparaben, ethylparaben, propylparaben such as sodium propylparaben, butylparaben or a combination of two or more thereof.

The oral levothyroxine solution may also comprise an excipient such as a polyol conferring sweetness to the solution, such as maltitol, xylitol or sorbitol or a combination of two or more thereof.

In a preferred embodiment, the oral Levothyroxine composition is packed in a unit dose system selected from the group consisting of ampoules, sachets, vials, blister packs, tubes, or stick packs. The unit dose can e.g. be arranged to deliver separate doses of levothyroxine from 25 up to 300 µg per single dose.

Further provided is an oral levothyroxine solution having a pH of 3.5-4.9, comprising 0.0004 to 0.004 w/v % levothyroxine or a salt thereof and 60 to 80 w/v % glycerol and water. The term w/v % corresponds to the weight in grams in a 100 ml solution. Such oral levothyroxine solution preferably comprises, after storage at 40° C. for at least 6 months, at least 93%, preferably at least 94% or at least 95% or even at least 96% of the levothyroxine as provided upon preparation of the solution. Attractively, the solution has a pH of 4.0-4.5. The solution particularly further comprises a preservative, in particular 0.03 to 0.1 w/v % of a preservative, in particular chosen from the group consisting of sodium benzoate, potassium benzoate, benzoic acid, sodium sorbate, potassium sorbate or sorbic acid.

Attractively, the oral levothyroxine compositions described herein can be used as a medicament, said medicament particularly being for the treatment of thyroid related disorders in a subject in need thereof, e.g. when the thyroid gland does not produce enough thyroid hormones that are required for normal growth and development of the body. Thyroid related disorders are e.g. selected from the group consisting of: hypothyroidism, goiter, and thyroid carcinoma.

The invention will now be illustrated by the following non-limiting examples.

EXAMPLES

As L-Thyroxine may degrade under the influence of light, the process was performed shielded from direct sunlight. The process was otherwise performed using regular manufacturing equipment. The basic steps are as follows:

Materials and Methods

Preparation of an Oral Levothyroxine Compositions

The following ingredients were used in the preparations described below:

L-thyroxine sodium salt (L-thyroxine Na) (Peptido GMBH, Germany)

Glycerol (glycerine 4808,99.5%, Oleon NV, Belgium)

Sodium methyl paraben (Sharon lab, Israel; Merck KGaA, Germany)

Benzoic acid (Carlo Erba, Italy)

Sorbic acid (Merck KGaA, Germany)

Potassium sorbate (Merck KGaA, Germany)

Sodium sorbate (Merck KGaA, Germany)

Sodium benzoate (Merck KGaA, Germany)

Potassium benzoate (Merck KGaA, Germany)

Citric acid (citric acid monohydrate BP98, Brenntag Nederland BV)

NaOH (sodium hydroxide pellets extra pure, Merck KGaA, Germany)

Propylene glycol (1,2-propylene glycol, BASF, Germany)

Maltitol solution (Maltilite 75/75 Pharma, Tereos Syral SAS, France; Lycasin 75/75, Roquette, France)

Sorbitol solution (PharmSorbidex NC® 16205, Cargill, Germany; Meritol 160 pharma, Syral, France; Neosorb 70/70 NB, Roquette, France)

Maltodextrin powder (glucidex 12D, Roquette, France; Maldex G120 pharma, Syral, France)

PEG liquid (polyglycol 400, Clariant, Germany)

Analytical Procedures

Appearance, Clarity and Degree of Opalesquence

Visual examination of the solution in an amber glass bottle according to the relevant Pharmacopoeia monograph: 'Clarity and Degree of Opalescence of Liquids' Ph. Eur. Cur. ed. (2.2.1).

pH Measurement pH value of the finished product is measured in accordance with Ph. Eur. Cur. ed. (2.2.3) using a calibrated pH-meter which is operated according to the manufacturer's instructions, such as the Martini Mi150 (Milwaukee, US). All measurements were made at ambient temperature.

A. Determination of Levothyroxine Content

Preparation

System

HPLC workstation (Shimadzu prominence series HPLC-DAD modular system consisting of: a DGU-20A5 mobile phase degasser a LC-20AD micro double piston pump, a SIL-20ACHT autosampler, a CTO-20AC column oven, a SPD-M20 UV/Vis photodiode arrasy detector and a personal computer with Shimadzu LC solutions software installed for the system control and the data record and process)

Reference Standards

Levothyroxine sodium EP CRS and Liothyronine sodium EP CRS

Diluent

Equal volumes of methanol and aq. 0.1 M sodium hydroxide solution

Levothyroxine Standard Solution

A quantity of levothyroxine sodium reference material equivalent to 20.0 mg of Levothyroxine sodium are dissolved in diluent and further diluted up to 100.0 ml final volume. 1.0 ml of the solution are further diluted to 50 ml with the same solvent.

Test Solution(s):

Dilute the finished drug product to final concentration of 4 µg/ml

Column:

Merck Lichrocart CN, 250×4.0 mm, 5 µm, or equivalent.

Column temperature:

Ambient

Flow rate:

1.0 ml/min

Mobile phase:

[Phosphoric acid 85%]/[Acetonitril]/[Water]=5/300/700 vol.

Injection volume:

50 µl

Detection:

UV 225 nm

Analysis time:

25 min

Measurement

System Suitability Solution:

Dissolve 20.0 mg of Liothyronine sodium reference material in diluent and further dilute up to 100.0 ml final volume. Transfer 5.0 µl of the solution of the final product containing 100.0 µg Levothyroxine sodium into a 10 ml volumetric flask. Dilute to volume with diluent.

Requirements:

a) The resolution between levothyroxine and liothyronie should be ≥4.0.

b) The symmetry factor of levothyroxine peak should be in the range of 0.8-1.5.

c) Repeatability (% RSD) of levothyroxine peak area should be not more than 1.7% (three replicates, n=3).

Procedure:

Separately inject the Test solutions and the Reference solutions, each solution in duplicates, alternatively. Record the chromatograms, and measure the responses (areas) for the major peaks.

Calculate the content of Levothyroxine sodium in the substance being examined.

Calculation

Content of Levothyroxine Sodium (Assay) in the Finished Drug Product

For percentage content of Levothyroxine sodium calculate using the formula:

$$\text{Content\_}(\%) = \frac{A_{test}}{A_{standard}} \times \frac{W_{std}}{20} \times \% \ P$$

where $A_{test}$: =The area of principal peak in the chromatogram of the test solution.

$A_{std}$: =The area of principal peak in the chromatogram of the standard solution.

$W_{std}$: =The accurate weight of Levothyroxine sodium reference material used for the preparation of standard solution (mg).

% P: =The % purity of Levothyroxine sodium reference material.

Average the result over all chromatograms recorded.

Each % recovery should be in the range of 98.0%-102.0% and the % RSD≤2.0%.

B. Determination of Related Substances

Preparation

System, reference standards, diluent, column, column temperature, flow rate, mobile phase and detection were as for the determination of levothyroxine.

Levothyroxine Reference Solutions

Reference Stock Solution 10.0 mg of Levothyroxine reference material 10.0 mg of liothyronine sodium reference material is dissolved in diluent in a final volume of 250 ml (40 µg/ml).

Reference solution (1%) for the presentations of 100 µg/5 ml and 50 µg/5 ml:

250 µl of the reference stock solution are further diluted to 100 ml with the same solvent (0.10 µg/ml).

Reference solution (1%) for the presentation of 25 µg/5 ml:

250 µl of the reference stock solution are further diluted to 200 ml with the same solvent (0.05 µg/ml).

Test Solutions:

Test solution for the presentation of 100 µg/5 ml:

Dilute 5.0 ml of the formulation with diluent up to 10 ml final volume (10 µg/ml).

Test solution for the presentation of 50 µg/5 ml:

Use the finished product as is (10 µg/ml).

Test solution for the presentation of 50 mcg/5 ml:

Use the finished product as is (5 µg/ml).

Injection Volume:

50 µl for the presentation of 100 µg/5 ml.

50 µl for the presentation of 50 µg/5 ml.

100 µl for the presentation of 25 µg/5 ml.

Analysis Time:

45 minutes.

Measurement

System Suitability Solution 1:

Dissolve 20.0 mg of Liothyronine sodium reference material in diluent and further dilute up to 100.0 ml final volume.

Transfer 5.0 µl of the solution of the final product containing 100.0 µg Levothyroxine sodium into a 10 ml volumetric flask. Dilute to volume with diluent Requirements:

a) The resolution between levothyroxine and liothyronie should be 4.0.

b) The symmetry factor of levothyroxine peak should be in the range of 0.8-1.5 c) Repeatability (% RSD) of levothyroxine peak area should be not more than 1.7% (three replicates, n=3.

System Suitability Solution 1:

Dilute 1 ml of the reference solution (1%) to 10 ml final volume with diluent.

Requirements:

Signal-to-noise ratio for the levothyroxine and liothyronine peaks should be not less than 10.

Procedure:

Separately inject the Test solutions and the Reference solutions, each solution in duplicates, alternatively. Record the chromatograms, and measure the responses (areas) for the major peaks.

Calculate the content of Levothyroxine sodium in the substance being examined.

Calculation

Content of Liothyronine in the Finished Drug Product

For percentage content of liothyronine calculate using the formulae:

$$\% \text{ Liothyronine} = \cdot \frac{A_{test\_A}}{A_{ref}} \cdot \times \cdot \frac{W'_{ref}}{10} \cdot \times \cdot 1.0\%$$

where $A_{test}$: =The area of liothyronine peak in the chromatogram of the test solution.

$A_{ref}$: =The area of liothyronine peak in the chromatogram of the liothyronine reference solution.

$W_{ref}$: =The accurate weight of liothyronine used for the preparation of standard solution (mg).

Average the result over all chromatograms recorded.

Content of any Unspecified Impurity in the Finished Drug Product

For percentage content of unspecified impurity calculate using the formulae:

$$\% \text{ Any} \cdot \text{impurity} = \cdot \frac{A_{test\_A}}{A_{ref}} \cdot \times \cdot \frac{W_{ref}}{10} \cdot \times \cdot 1.0\%$$

where $A_{test}$: =The area of any impurity peak in the chromatogram of the test solution.

$A_{ref}$: =The area of levothyroxine peak in the chromatogram of the reference solution.

$W_{ref}$: =The accurate weight of levothyroxine used for the preparation of standard solution (mg).

Average the result over all chromatograms recorded.

Acceptance Criteria

Each % recovery should be in the range of 95.0-105.0% and the % RSD≤5.0%.

Experimentals

Preparation GL-H1P 20 g of glycerol was mixed with 3 ml water. To the said mixture, 21 mg of the sodium salt of L-thyroxine (L-thyroxine Na) was added and the mixture was stirred using a laboratory mixer (Ika mixer, Eurostar 40 digital) at 600 rpm while being heated to 45° C. until a homogenous suspension was obtained.

At ambient temperature, the suspension was added to 350 ml water that was previously brought at pH 10 by an aqueous NaOH solution (2.5 w/w %), whereafter 5 g paraben was added, followed by stirring using the same laboratory mixer as above at 400 rpm at ambient temperature until a clear solution was obtained.

To the solution, 685 g of glycerol was added, and the pH was adjusted to envisaged values (each value chosen between 3.5 and 7.5) using an aqueous citric acid solution (50 w/w %). If necessary, the volume was adjusted to a L-thyroxine concentration of 100 µg/5 ml.

Preparation GL-H1S 20 g of glycerol was mixed with 3 ml water. To the said mixture, 21 mg of the sodium salt of L-thyroxine (L-thyroxine Na) was added and the mixture was stirred using a laboratory mixer (Ika mixer, Eurostar 40 digital) at 600 rpm while being heated to 45° C. until a homogenous suspension was obtained.

At ambient temperature, the suspension was added to 250 ml water that was previously brought at pH 10 by an aqueous NaOH solution (2.5 w/w %). To a separate container, 2.5 g of sorbic acid was added to 300 g of glycerol and 100 ml of water, followed by stirring and heating to 70° C. using the same laboratory mixer as above at 400 rpm until a clear solution was obtained. Subsequently, the solution was cooled down to ambient temperature and combined with the above homogenous suspension.

To the above combined suspension, 385 g of glycerol was added, and the pH was adjusted to envisaged values (each value chosen between 3.5 and 5.5) using an aqueous citric acid solution (50 w/w %). If necessary, the volume was adjusted to a L-thyroxine concentration of 100 µg/5 ml.

Preparation GL-C1S

The same protocol as for preparation GL-H1S1 was followed, however 3.3 g of potassium sorbate was used instead of sorbic acid, and no heating was performed while dissolving the preservative. All steps were performed at ambient temperature, i.e. at 18-21° C.

Preparation GL-H1B 20 g of glycerol was mixed with 3 ml water. To the said mixture, 21 mg of the sodium salt of L-thyroxine (L-thyroxine Na) was added and the mixture was stirred using a laboratory mixer (Ika mixer, Eurostar 40 digital) at 600 rpm while being heated to 45° C. until a homogenous suspension was obtained.

At ambient temperature, the suspension was added to 250 ml water that was previously brought at pH 10 by an aqueous NaOH solution (2.5 w/w %).

To a separate container, 1.25 g of benzoic acid was added to 100 ml of water, followed by stirring and heating to 85-90° C. using the same laboratory mixer as above at 400 rpm until a clear solution was obtained. Subsequently, the solution was cooled down to ambient temperature and combined with the above homogenous suspension.

To the above combined suspension, 685 g of glycerol was added, and the pH was adjusted to envisaged values (each value chosen between 3.5 and 4.8) using an aqueous citric acid solution (50 w/w %). If necessary, the volume was adjusted to a L-thyroxine concentration of 100 µg/5 ml.

Preparation GL-C1B

The same protocol as for preparation GL-H1B was followed, however 1.5 g of sodium benzoate was used instead of benzoic acid, and no heating was performed while dissolving the preservative. All steps were performed at ambient temperature, i.e. at 18-21° C.

Preparation GL-C1P

The same protocol as for preparation GL-H1P was followed, however without heating. All steps were performed at ambient temperature, i.e. at 18-21° C.

Preparation GL-H2P

The same protocol as for preparation GL-H1P was followed, except that the Levothyroxine was mixed with 20 g glycerol without being mixed with 3 ml water.

Preparation GL-C2P

The same protocol as for preparation GL-H2P was followed, however without heating. All steps were performed at ambient temperature, i.e. at 18-21° C.

Preparation GL-H3P

The same protocol as for preparation GL-H2P was followed, except that the suspension was added to 350 ml water of neutral pH, followed by additional mixing to result in an homogenous suspension. The pH of the said suspension was adjusted to pH 10 by admixing an aqueous NaOH solution (2.5 w/w %), whereafter the paraben was added.

Preparation GL-C3P

The same protocol as for preparation GL-H3P was followed, however without heating. All steps were performed at ambient temperature, i.e. at 18-21° C.

Preparation GL-H4P

The same protocol as for preparation GL-H1P was followed, except that the glycerol was mixed with 20 ml water before the levothyroxine was added. To compensate for the volume increase, the suspension was added to 330 ml water having a pH of 10.

Preparation GL-C4P

The same protocol as for preparation GL-H4P was followed, however without heating. All steps were performed at ambient temperature, i.e. at 18-21° C.

Preparation GL-H5P 350 ml water that was previously brought at pH 10 by an aqueous NaOH solution (2.5 w/w %) was mixed with 21 mg levothyroxine, and the mixture was stirred using a laboratory mixer (Ika mixer, Eurostar 40 digital) at 600 rpm while being heated to 45° C. until a clear solution was obtained. 5 g paraben was added, followed by stirring using the same laboratory mixer as above at 400 rpm at ambient temperature and addition of 705 g glycerol, resulting in a clear solution. The pH was adjusted to the envisaged value using an aqueous citric acid solution (50 w/w %).

Preparation GL-C5P

The same protocol as for preparation GL-H5P was followed, however without heating. All steps were performed at ambient temperature, i.e. at 18-21° C.

Preparation GLPEG-H1P 20 g of a 10:2 mixture (on weight basis) of glycerol and polyethylene glycol 400 was mixed with 3 ml water. To the said mixture, 21 mg of the sodium salt of L-thyroxine (L-thyroxine Na) was added and the mixture was stirred using a laboratory mixer (Ika mixer, Eurostar 40 digital) at 600 rpm while being heated to 45° C. until a homogenous suspension was obtained.

At ambient temperature, the suspension was added to 350 ml water that was previously brought at pH 10 by an aqueous NaOH solution (2.5 w/w %), whereafter 5 g paraben was added, followed by stirring using the same laboratory mixer as above at 400 rpm at ambient temperature until a clear solution was obtained.

To the solution, 685 g of glycerol was added, and the pH was adjusted to the envisaged value using an aqueous citric acid solution (50 w/w %).

Preparation GLPEG-C1P

The same protocol as for preparation GLPEG-H1P was followed, however without heating. All steps were performed at ambient temperature, i.e. at 18-21° C.

Preparation PG-H1P

The same protocol as for preparation GL-H1P was followed, wherein glycerol was replaced by propylene glycol.

Preparation PG-C1P

The same protocol as for preparation PG-H1P was followed, however without heating. All steps were performed at ambient temperature, i.e. at 18-21° C.

Preparation MTL-H1P 20 ml of an aqueous solution of maltitol (725 g/l) was mixed with 21 mg of the sodium salt of L-thyroxine (L-thyroxine Na) and the mixture was stirred using a laboratory mixer (manufacturer, type) at 600 rpm while being heated to 45° C. until a homogenous suspension was obtained.

At ambient temperature, the suspension was added to 350 ml of the maltitol solution (725 g/l) that was previously brought at pH 10 by an aqueous NaOH solution (2.5 w/w %), whereafter 18 g propylene glycol and 1.8 g paraben was added, followed by stirring using the same laboratory mixer as above at 400 rpm at ambient temperature until a clear solution was obtained.

To the solution, 550 ml of the above aqueous maltitol solution (725 g/l) was added, and the pH was adjusted to the envisaged value using an aqueous citric acid solution (50 w/w %).

Preparation MTL-C1P

The same protocol as for preparation MTL-H1P was followed, however without heating. All steps were performed at ambient temperature, i.e. at 18-21° C.

Preparation SB-H1P 23 ml of an aqueous solution of sorbitol (550 g/l) was mixed with 21 mg of the sodium salt of L-thyroxine (L-thyroxine Na) and the mixture was stirred using a laboratory mixer (Ika mixer, Eurostar 40 digital) at 600 rpm while being heated to 45° C. until a homogenous suspension was obtained.

At ambient temperature, the suspension was added to 350 ml of the sorbitol solution that was previously brought at pH 10 by an aqueous NaOH solution (2.5 w/w %), whereafter 5 g paraben was added, followed by stirring using the same laboratory mixer as above at 400 rpm at ambient temperature until a clear solution was obtained.

To the solution, 550 ml of the sorbitol solution was added, and the pH was adjusted to the envisaged value using an aqueous citric acid solution (50 w/w %).

Preparation SB-C1P

The same protocol as for preparation SB-H1P was followed, however without heating. All steps were performed at ambient temperature, i.e. at 18-21° C.

Preparation MTX-H1P 23 ml of an aqueous solution of maltodextrin (600 g/l) was mixed with 21 mg of the sodium salt of L-thyroxine (L-thyroxine Na) and the mixture was stirred using a laboratory mixer (Ika mixer, Eurostar 40 digital) at 600 rpm while being heated to 45° C. until a homogenous suspension was obtained.

At ambient temperature, the suspension was added to 350 ml of the maltodextrin solution that was previously brought at pH 10 by an aqueous NaOH solution (2.5 w/w %), whereafter 5 g paraben was added, followed by stirring using the same laboratory mixer as above at 400 rpm at ambient temperature until a clear solution was obtained.

To the solution, 685 g of the maltodextrin solution was added, and the pH was adjusted to the envisaged value using an aqueous citric acid solution (50 w/w %).

Preparation MTX-C1P

The same protocol as for preparation MTX-H1P was followed, however without heating. All steps were performed at ambient temperature, i.e. at 18-21° C.

Preparation GL-C1BB

For a 2 L solution, 735,633 ml purified water, 0.6 g trisodium citrate and 1.20 g sodium benzoate were mixed at ambient temperature. The solution was brought to a pH of 9.8-10.5 by the addition of 2.5 w/v % NaOH. 1569.5 g glycerol 99% was added and allowed to mix for 20 minutes at ambient temperature. 0.044 g levothyroxine sodium was added, and mixing was performed for 30 minutes at ambient temperature. 2.35 g anhydrous citric acid was added to arrive at a pH of 4.0 after mixing for 10 minutes at ambient temperature. Water was added until a total volume of 2 L was obtained (up to about 30 ml).

Comparative Stability Tests:

The stability of the solutions was tested against oral levothyroxine compositions described in WO2012/120338 containing 20 μg/ml of levothyroxine sodium (100 μg/5 ml solution) and having a final pH between 5-6, and additional controls having a pH of 6.5-7.5.

Tables 1A-C and 2 show analytical results of the levothyroxine solutions GL-H1P, GL-H1S, GL-H1B and GL-C1P, respectively, having a pH of 3.5 to 7.5 after 3 and 6 months storage at ambient conditions without being refrigerated before the storage. Samples having a pH of 5 to 7.5 are comparable examples; those having a pH of 5-6 are as described in WO2012/120338. The stability of the solutions is evaluated by the content of levothyroxine sodium, the content of liothyronine, and the content of other impurities present in the composition after the storage period. The numbers in the tables are relative weight percentages based on the initial levothyroxine content as determined directly after preparation.

As can be seen in tables 1A-1C, preservatives paraben, sorbic acid and benzoic acid give comparable results with regard to stability of Levothyroxine. Sorbic acid and Benzoic acid give a slightly better value at a pH of 4.5, whereas paraben has better values at other pH values. Values obtained for samples GL-C1S, prepared with potassium sorbate without heating, and GL-C1B prepared with sodium benzoate without heating, had similar results as for the sorbic acid and benzoic acid samples respectively.

TABLE 1A

GL-H1P samples, stored for 0, 3 or 6 months at 40° C.

| | Months | | | | | | | | | | | |
|---|---|---|---|---|---|---|---|---|---|---|---|---|
| | 0 | 3 | 6 | 0 | 3 | 6 | 0 | 3 | 6 | 0 | 3 | 6 |
| pH | Levothyroxine sodium (95-105%) | | | Liothyronine (NMT 2.00%) | | | Single unknown impurities (NMT 1.00%) | | | Total other unspecified impurities (NMT 2.00%) | | |
| 3.5 | 100.5 | 98.3 | 94.0 | 0.13 | 0.71 | 1.17 | <0.05 | 1.46 | 0.63 | <0.05 | 3.35 | 5.79 |
| 4.0 | 101.1 | 98.2 | 96.3 | 0.13 | 1.00 | 1.41 | <0.05 | 0.27 | 0.42 | <0.05 | 0.7 | 0.71 |
| 4.5 | 101.4 | 98.5 | 94.1 | 0.13 | 1.56 | 3.83 | <0.05 | 0.50 | 0.55 | <0.05 | 1.07 | 0.55 |
| 4.8 | 101.2 | 97 | 95 | 0.13 | 1.48 | 2.89 | <0.05 | 0.48 | 0.53 | <0.05 | 1.05 | 0.7 |
| 5.0 | 101.0 | 96.1 | 92.1 | 0.14 | 1.98 | 4.1 | <0.05 | 0.61 | 0.63 | <0.05 | 1.32 | 1.11 |
| 5.5 | 101.2 | 96.6 | 89.8 | 0.14 | 2.49 | 6.03 | <0.05 | 0.86 | 0.77 | <0.05 | 1.99 | 0.77 |
| 6.0 | 100.8 | 94 | 89.1 | 0.10 | 2.78 | 6.48 | <0.05 | 1.25 | 2.4 | <0.05 | 2.3 | 3.3 |
| 6.5 | 100.9 | 89.5 | 86 | 0.15 | 4.07 | 6.54 | <0.05 | 2.10 | 2.8 | <0.05 | 2.99 | 3.9 |
| 7.0 | 100.6 | 84 | 91.3 | 0.13 | 4.12 | 6.91 | <0.05 | 2.4 | 3.4 | <0.05 | 3.55 | 4.23 |
| 7.5 | 100.5 | 82.6 | 80.0 | 0.16 | 4.62 | 7.31 | 0.12 | 2.11 | 3.5 | 0.12 | 4.14 | 4.3 |

TABLE 1B

GL-H1S samples, stored for 0, 3 or 6 months at 40° C.

| | Months | | | | | | | | | | | |
|---|---|---|---|---|---|---|---|---|---|---|---|---|
| | 0 | 3 | 6 | 0 | 3 | 6 | 0 | 3 | 6 | 0 | 3 | 6 |
| pH | Levothyroxine sodium (95-105%) | | | Liothyronine (NMT 2.00%) | | | Single unknown impurities (NMT 1.00%) | | | Total other unspecified impurities (NMT 2.00%) | | |
| 3.5 | 100.0 | 96.5 | 92.1 | 0.13 | 0.88 | 2.1 | <0.05 | 1.75 | 1.2 | <0.05 | 3.9 | 6.01 |
| 4.0 | 100.1 | 98.1 | 96.1 | 0.13 | 1.2 | 1.45 | <0.05 | 0.61 | 0.65 | <0.05 | 0.81 | 0.82 |
| 4.5 | 100.4 | 96.6 | 94.5 | 0.13 | 1.7 | 3.88 | <0.05 | 0.77 | 0.78 | <0.05 | 1.2 | 1.21 |
| 4.8 | 100.3 | 95.5 | 94.1 | 0.13 | 1.75 | 4.1 | <0.05 | 0.82 | 0.88 | <0.05 | 1.5 | 1.56 |
| 5.0 | 100.9 | 96 | 92.0 | 0.14 | 2.2 | 4.8 | <0.05 | 0.91 | 0.99 | <0.05 | 1.61 | 1.61 |
| 5.5 | 101.1 | 95.5 | 87.5 | 0.14 | 3.6 | 7.1 | <0.05 | 1.2 | 1.6 | <0.05 | 2.2 | 2.3 |

TABLE 1C

GL-H1B samples, stored for 0, 3 or 6 months at 40° C.

| | | | | | | | Months | | | | | |
|---|---|---|---|---|---|---|---|---|---|---|---|---|
| | 0 | 3 | 6 | 0 | 3 | 6 | 0 | 3 | 6 | 0 | 3 | 6 |
| pH | Levothyroxine sodium (95-105%) | | | Liothyronine (NMT 2.00%) | | | Single unknown impurities (NMT 1.00%) | | | Total other unspecified impurities (NMT 2.00%) | | |
| 3.5 | 100.1 | 97.5 | 93.8 | 0.13 | 0.81 | 1.23 | <0.05 | 1.65 | 1.01 | <0.05 | 3.6 | 6.01 |
| 4.0 | 100.1 | 98.0 | 95.6 | 0.13 | 1.1 | 1.5 | <0.05 | 0.51 | 0.61 | <0.05 | 0.82 | 0.85 |
| 4.5 | 100.3 | 97.4 | 94.8 | 0.13 | 1.65 | 4.01 | <0.05 | 0.7 | 0.77 | <0.05 | 1.2 | 1.1 |
| 4.8 | 100.4 | 96.5 | 93.5 | 0.14 | 1.71 | 3.5 | <0.05 | 0.8 | 0.85 | <0.05 | 1.3 | 1.2 |

TABLE 2

GL-C1P samples, stored for 0, 3 or 6 months at 40° C.

| | | | | | | | Months | | | | | |
|---|---|---|---|---|---|---|---|---|---|---|---|---|
| | 0 | 3 | 6 | 0 | 3 | 6 | 0 | 3 | 6 | 0 | 3 | 6 |
| pH | Levothyroxine sodium (95-105%) | | | Liothyronine (NMT 2.00%) | | | Single unknown impurities (NMT 1.00%) | | | Total other unspecified impurities (NMT 2.00%) | | |
| 3.5 | 100.5 | 95.4 | 93.4 | 0.11 | 0.56 | 0.89 | 0.11 | 1.68 | 0.76 | 0.11 | 2.86 | 3.01 |
| 4.0 | 100.8 | 96.6 | 94.2 | 0.13 | 1.01 | 1.92 | <0.05 | 0.31 | 0.47 | <0.05 | 0.61 | 0.72 |
| 4.5 | 101.1 | 96.8 | 92.8 | 0.14 | 1.39 | 3.34 | <0.05 | 0.48 | 0.53 | <0.05 | 0.91 | 0.61 |
| 4.8 | 101.0 | 96.0 | 92.0 | 0.13 | 1.45 | 3.50 | <0.05 | 0.50 | 0.55 | <0.05 | 0.92 | 0.61 |
| 5.0 | 101.0 | 95.2 | 90.2 | 0.13 | 1.90 | 4.79 | <0.05 | 0.56 | 0.62 | <0.05 | 1.21 | 0.62 |
| 5.5 | 104.4 | 93.8 | 87.9 | 0.14 | 2.37 | 5.87 | <0.05 | 0.93 | 0.77 | <0.05 | 1.85 | 0.77 |
| 6.0 | 100.8 | 93.0 | 90.0 | 0.14 | 2.84 | 6.51 | <0.05 | 1.17 | 2.3 | <0.05 | 2.20 | 3.2 |
| 6.5 | 104.2 | 89.3 | 86.1 | 0.15 | 3.74 | 6.3 | <0.05 | 1.93 | 2.7 | <0.05 | 2.90 | 3.5 |
| 7.0 | 100.6 | 84.7 | 82.3 | 0.16 | 4.13 | 7.1 | <0.05 | 2.22 | 3.1 | <0.05 | 3.43 | 4.1 |
| 7.5 | 103.5 | 83.2 | 80.1 | 0.16 | 4.18 | 7.2 | 0.16 | 2.12 | 3.0 | 0.16 | 3.34 | 4.2 |

The results showed that at low pH between 3.5 and 4.8, the solutions are more stable at 40° C. as compared to higher pH, in particular after storage of 6 months. When the solution is prepared without heating (table 2A) slightly less impurities are observed as compared to the solution prepared using heating (table 1A). In particular, solutions having a pH of 4.0-4.5 show improved stability and less liothyronine and less impurities.

Similar results as for GL-H1P were obtained for GL-H2P to GL-H5P. The same is true for the corresponding samples, prepared without heat. This means that the order of adding the different components does not have a significant effect.

It can be seen from table 3 that at a pH of below 5, i.e. of 4.9 or less, improved stability and less impurities are observed after 6 months of storage at 40° C. After 6 months of storage, the samples having a pH of 4.8 and below have a better stability. Similar results were obtained for samples prepared without heat, where again, less impurities were observed as compared to corresponding samples prepared using heat.

TABLE 3

GLPEG-H1P samples, stored for 0, 3 or 6 months at 40° C.

| | | | | | | | Months | | | | | |
|---|---|---|---|---|---|---|---|---|---|---|---|---|
| | 0 | 3 | 6 | 0 | 3 | 6 | 0 | 3 | 6 | 0 | 3 | 6 |
| pH | Levothyroxine sodium (95-105%) | | | Liothyronine (NMT 2.00%) | | | Single unknown impurities (NMT 1.00%) | | | Total other unspecified impurities (NMT 2.00%) | | |
| 3.5 | 108.9 | 102.0 | 99.3 | 0.12 | 0.80 | 1.2 | 0.20 | 1.98 | 1.2 | 0.20 | 1.60 | 2.4 |
| 4.0 | 108.1 | 102.1 | 100.2 | 0.11 | 1.10 | 1.51 | 0.21 | 1.01 | 1.48 | 0.21 | 1.54 | 2.6 |
| 4.5 | 108.5 | 101.3 | 98.6 | 0.12 | 1.04 | 2.94 | 0.24 | 1.19 | 1.56 | 0.24 | 1.80 | 2.9 |
| 4.8 | 108.2 | 101 | 98.5 | 0.13 | 1.02 | 2.90 | 0.29 | 2.15 | 1.50 | 0.29 | 2.67 | 3.1 |
| 5.0 | 108.4 | 101.3 | 99.6 | 0.12 | 0.82 | 3.2 | 0.29 | 1.67 | 1.61 | 0.29 | 2.28 | 3.2 |
| 5.5 | 108.4 | 104.1 | 94.5 | 0.12 | 0.72 | 4.08 | 0.27 | 1.02 | 1.67 | 0.27 | 2.64 | 3.5 |
| 6.0 | 108.0 | 98.2 | 92.3 | 0.14 | 0.60 | 5.5 | 0.29 | 0.43 | 2.1 | 0.29 | 2.84 | 3.8 |
| 6.5 | 108.0 | 97.1 | 91.5 | 0.14 | 1.50 | 6.01 | 0.25 | 0.98 | 3.1 | 0.25 | 2.68 | 4.1 |
| 7.0 | 108.2 | 95.2 | 89.1 | 0.13 | 2.50 | 6.2 | 0.19 | 1.20 | 3.5 | 0.19 | 2.65 | 4.5 |
| 7.5 | 108.2 | 89.2 | 84.3 | 0.14 | 3.80 | 6.4 | 0.11 | 2.50 | 3.7 | 0.11 | 3.30 | 4.7 |

TABLE 4

PG-H1P samples, stored for 0, 3 or 6 months at 40° C.

| | Months | | | | | | | | | | | |
|---|---|---|---|---|---|---|---|---|---|---|---|---|
| | 0 | 3 | 6 | 0 | 3 | 6 | 0 | 3 | 6 | 0 | 3 | 6 |
| pH | Levothyroxine sodium (95-105%) | | | Liothyronine (NMT 2.00%) | | | Single unknown impurities (NMT 1.00%) | | | Total other unspecified impurities (NMT 2.00%) | | |
| 3.5 | 100.6 | 96.5 | 93.4 | 0.12 | 0.83 | 1.20 | <0.05 | 1.43 | 0.90 | <0.05 | 3.10 | 3.2 |
| 4.0 | 100.7 | 97.2 | 94.5 | 0.14 | 1.20 | 2.01 | <0.05 | 0.55 | 0.60 | <0.05 | 0.70 | 1.1 |
| 4.5 | 101.3 | 96.5 | 94.0 | 0.14 | 1.45 | 3.55 | <0.05 | 0.60 | 0.67 | <0.05 | 1.10 | 1.2 |
| 4.8 | 101.2 | 96.0 | 92.0 | 0.14 | 2.20 | 4.05 | <0.05 | 0.70 | 0.67 | <0.05 | 1.20 | 1.2 |
| 5.0 | 101.2 | 95.1 | 90.1 | 0.14 | 3.30 | 6.01 | <0.05 | 0.60 | 0.77 | <0.05 | 1.51 | 1.3 |
| 5.5 | 104.6 | 94.1 | 88.2 | 0.15 | 3.20 | 7.03 | <0.05 | 1.10 | 0.88 | <0.05 | 1.95 | 0.9 |
| 6.0 | 100.9 | 93.0 | 83.1 | 0.14 | 4.22 | 7.44 | <0.05 | 1.30 | 2.40 | <0.05 | 2.50 | 2.3 |
| 6.5 | 104.1 | 85.1 | 82.1 | 0.15 | 4.24 | 7.55 | <0.05 | 2.22 | 2.9 | <0.05 | 3.1 | 3.6 |
| 7.0 | 100.0 | 84.2 | 81.7 | 0.16 | 5.01 | 8.01 | <0.05 | 3.2 | 3.2 | <0.05 | 3.6 | 3.6 |
| 7.5 | 102.1 | 84.3 | 79.3 | 0.17 | 5.02 | 8.1 | 0.11 | 3.7 | 3.5 | 0.11 | 3.6 | 4.1 |

From table 4 it is clear that propylene glycol as solvent results in acceptable stability of levothyroxine, in particular at a pH of 4.8 or below. Similar results were obtained for samples prepared without heat, where again, less impurities were observed as compared to corresponding samples prepared using heat.

Similar experiments were performed using other organic solvents, such as those mentioned in the description, resulted in similar data.

TABLE 5

MTL-H1P samples, stored for 0, 3 or 6 months at 40° C.

| | Months | | | | | | | | | | | |
|---|---|---|---|---|---|---|---|---|---|---|---|---|
| | 0 | 3 | 6 | 0 | 3 | 6 | 0 | 3 | 6 | 0 | 3 | 6 |
| pH | Levothyroxine sodium (95-105%) | | | Liothyronine (NMT 2.00%) | | | Single unknown impurities (NMT 1.00%) | | | Total other unspecified impurities (NMT 2.00%) | | |
| 3.5 | 100.5 | 95.0 | 92.1 | 0.12 | 0.7 | 1.1 | <0.05 | 0.7 | 0.9 | <0.05 | 1.0 | 0.4 |
| 4.0 | 100.5 | 96.0 | 93.2 | 0.13 | 1.2 | 2.5 | <0.05 | 0.4 | 0.6 | <0.05 | 1.1 | 0.5 |
| 4.5 | 100.9 | 97.0 | 91.5 | 0.13 | 1.5 | 3.9 | <0.05 | 0.8 | 0.9 | <0.05 | 1.1 | 1.7 |
| 4.8 | 100.8 | 97.0 | 89.5 | 0.14 | 1.7 | 4.2 | <0.05 | 1.0 | 1.1 | <0.05 | 1.3 | 1.8 |
| 5.0 | 101.0 | 96.0 | 86.0 | 0.14 | 2.0 | 5.1 | <0.05 | 1.8 | 2.0 | <0.05 | 1.7 | 1.9 |
| 5.5 | 100.8 | 95.0 | 85.2 | 0.15 | 2.4 | 6.1 | <0.05 | 2.0 | 2.1 | <0.05 | 2.0 | 1.1 |
| 6.0 | 100.7 | 94.5 | 84.1 | 0.15 | 3.3 | 6.5 | <0.05 | 2.5 | 1.5 | <0.05 | 2.5 | 1.4 |
| 6.5 | 100.3 | 88.3 | 83.2 | 0.16 | 4.6 | 7.2 | <0.05 | 4.1 | 3.1 | <0.05 | 4.1 | 3.2 |
| 7.0 | 100.0 | 85.9 | 80.1 | 0.16 | 5.1 | 7.8 | <0.05 | 4.4 | 3.8 | <0.05 | 4.4 | 3.8 |
| 7.5 | 100.1 | 83.5 | 79.4 | 0.17 | 5.3 | 7.9 | 0.10 | 3.8 | 4.1 | 0.10 | 4.0 | 4.1 |

Using a maltitol solution, increased stability was observed at a pH of 4.8 or less, resulting in less impurities. Similar results were obtained for samples prepared without heat, where again, less impurities were observed as compared to corresponding samples prepared using heat.

TABLE 6

SB-H1P samples, stored for 0, 3 or 6 months at 40° C.

| | Months | | | | | | | | | | | |
|---|---|---|---|---|---|---|---|---|---|---|---|---|
| | 0 | 3 | 6 | 0 | 3 | 6 | 0 | 3 | 6 | 0 | 3 | 6 |
| pH | Levothyroxine sodium (95-105%) | | | Liothyronine (NMT 2.00%) | | | Single unknown impurities (NMT 1.00%) | | | Total other unspecified impurities (NMT 2.00%) | | |
| 3.5 | 101.2 | 85 | 80.1 | 0.13 | 1.2 | 1.4 | <0.05 | 1.2 | 1.5 | <0.05 | 1.5 | 1.7 |
| 4.0 | 100.8 | 81 | 75.6 | 0.13 | 1.6 | 1.7 | <0.05 | 1.5 | 1.7 | <0.05 | 1.3 | 1.4 |
| 4.5 | 100.1 | 80 | 75.1 | 0.13 | 2.3 | 2.6 | <0.05 | 1.9 | 2.2 | <0.05 | 1.2 | 1.6 |
| 4.8 | 100.3 | 80 | 75 | 0.13 | 2.31 | 3.1 | <0.05 | 1.95 | 2.6 | <0.05 | 1.25 | 2.1 |
| 5.0 | 100.7 | 72 | 68 | 0.14 | 2.21 | 3.2 | <0.05 | 2 | 2.7 | <0.05 | 1.8 | 2.3 |
| 5.5 | 100.8 | 70 | 65.5 | 0.14 | 2.4 | 4.1 | <0.05 | 2.1 | 3.1 | <0.05 | 2 | 2.5 |
| 6.0 | 100.7 | 52 | 47.2 | 0.14 | 2.2 | 5.1 | <0.05 | 2.7 | 3.1 | <0.05 | 2.6 | 3.5 |
| 6.5 | 100.8 | 62 | 55.1 | 0.15 | 3.5 | 6.5 | <0.05 | 5 | 4.1 | <0.05 | 3.5 | 4.2 |
| 7.0 | 100.5 | 63 | 55 | 0.15 | 8 | 7.5 | <0.05 | 6.3 | 6.6 | <0.05 | 6.3 | 6.8 |
| 7.5 | 100.7 | 62 | 54.1 | 0.16 | 8 | 7.7 | 0.13 | 5.2 | 6.7 | 0.13 | 5 | 6.1 |

Using a sorbitol solution, increased stability was observed at a pH of 4.8 or less, resulting in less impurities, both after 3 months and 6 months of storage. Similar results were obtained for samples prepared without heat, where again, less impurities were observed as compared to corresponding samples prepared using heat.

TABLE 7

MTX-H1P samples, stored for 0, 3 or 6 months at 40° C.

| | Months | | | | | | | | | | | |
|---|---|---|---|---|---|---|---|---|---|---|---|---|
| | 0 | 3 | 6 | 0 | 3 | 6 | 0 | 3 | 6 | 0 | 3 | 6 |
| | | | | | | | | Single unknown impurities | | | Total other unspecified impurities | |
| | Levothyroxine | | | Liothyronine | | | impurities | | | impurities | | |
| pH | sodium (95-105%) | | | (NMT 2.00%) | | | (NMT 1.00%) | | | (NMT 2.00%) | | |
| 3.5 | 101.0 | 96.2 | 92.1 | 0.12 | 2 | 2.2 | <0.05 | 0.5 | 0.7 | <0.05 | 1 | 1.2 |
| 4.0 | 100.7 | 96.0 | 92 | 0.13 | 1.8 | 2.3 | <0.05 | 0.5 | 0.8 | <0.05 | 1 | 1.3 |
| 4.5 | 100.3 | 95.9 | 90.2 | 0.43 | 4.6 | 5.1 | <0.05 | 0.6 | 0.9 | <0.05 | 1.5 | 1.7 |
| 4.8 | 100.5 | 95.2 | 89.5 | 0.13 | 4.7 | 5.6 | <0.05 | 0.5 | 0.9 | <0.05 | 1.4 | 1.8 |
| 5.0 | 100.6 | 97.8 | 92.5 | 0.14 | 3.8 | 5.2 | <0.05 | 0.4 | 0.8 | <0.05 | 1 | 1.7 |
| 5.5 | 100.3 | 98.4 | 93.2 | 0.13 | 3.5 | 5 | <0.05 | 0.4 | 0.8 | <0.05 | 0.9 | 1.7 |
| 6.0 | 100.4 | 98.9 | 91.2 | 0.14 | 4.1 | 6.1 | <0.05 | 0.5 | 0.7 | <0.05 | 1.3 | 2.1 |
| 6.5 | 100.4 | 90.2 | 85.2 | 0.15 | 4.2 | 7.2 | <0.05 | 0.7 | 1.1 | <0.05 | 1.6 | 2.2 |
| 7.0 | 100.5 | 88.5 | 83.1 | 0.15 | 5.2 | 7.6 | <0.05 | 0.9 | 1.2 | <0.05 | 2.1 | 2.6 |
| 7.5 | 100.6 | 87.1 | 81.1 | 0.14 | 6.1 | 8 | 0.11 | 1.2 | 1.6 | 0.11 | 2.2 | 2.7 |

Using a maltodextrin solution, increased stability was observed after 6 months at a pH of 4.8 or less, resulting in less impurities. However, after 3 months of storage, solutions having a pH of 5-6 seem to be somewhat more stable. Similar results were obtained for samples prepared without heat, where again, less impurities were observed as compared to corresponding samples prepared using heat.

Similar samples were prepared with xylitol and mannitol, but below a pH of 6.5, precipitation was observed during or shortly after finalizing the preparation of the solution, and testing with these sugar alcohols was discontinued.

TABLE 8

GL-C1BB sample, stored for 0, 3 or 6 months at 40° C.

| | Months | | | | | | | | |
|---|---|---|---|---|---|---|---|---|---|
| | 0 | 3 | 6 | 0 | 3 | 6 | 0 | 3 | 6 |
| | % Levothyroxine sodium | | | % Liothyronine | | | % total of Single unknown impurities | | |
| pH | (95-105%) | | | (NMT 2.00%) | | | (NMT 2.00%) | | |
| 4.0 | 99.9 | 98.8 | 93.1 | 0.22 | 0.42 | 0.60 | <0.05 | 0.32 | 0.42 |

A stable solution of a pH of 4.0 was obtained with sodium benzoate as preservative and a citric acid-sodium citrate buffer.

TABLE 9

Solutions 1 and 2 of U.S. Pat. No. 9,345,722 and GL-H1p and GL-H1B, stored for 0 or 1 month at 40° C.

| | Sample 1 U.S. Pat. No. 9,345,722 | | Sample 1 U.S. Pat. No. 9,345,722 | | GL-H1P | | GL-H1B | | | |
|---|---|---|---|---|---|---|---|---|---|---|
| | | | | | Months | | | | | |
| | 0 | 1 | 0 | 1 | 0 | 1 | 0 | 1 | 0 | 1 |
| Levothyroxine sodium (95-105%) | 111.2 | 103.2 | 108.5 | 101.5 | 100.8 | 98 | 101.1 | 100.1 | 100.1 | 99.1 |
| Liothyronine (NMT 2.00%) | 0.14 | 0.30 | 0.13 | 0.32 | 0.13 | 0.30 | 0.13 | 0.18 | 0.13 | 0.25 |
| pH | 6.0 | 5.3 | 5.5 | 5.3 | 6.0 | 6.0 | 4.0 | 4.0 | 4.0 | 4.0 |

It is observed that the solutions of U.S. Pat. No. 9,345,722 are significantly less stable already after one months as compared to the samples of the invention GL-H1P and GL-H1B, both having a pH of 4.0. As a comparison, sample GL-H1P having a pH of 6.0 is shown, that is also more stable than both samples 1 and 2 of U.S. Pat. No. 9,345,722.

Preservation Efficacy Tests

Samples GL-C1P having a pH of 4.0 and 4.5, and samples GL-H1B,

GL-C1BB and GL-H1S, each having a pH of 4.0 were tested for efficacy of antimicrobial preservation according to the teaching of the European Pharmacopeia 9.0, section 5.1.3, pp 577 ff. As comparison, sample 1 of U.S. Pat. No. 9,345,722 has been prepared, in accordance with example 6 of U.S. Pat. No. 9,345,722. The test consists of challenging the sample solution with a prescribed inoculum of suitable micro-organisms as shown in the tables 10A-F, storing the inoculated solution at ambient temperature, avoiding sunlight, withdrawing samples from the container at specified intervals of time and counting the micro-organisms in the samples so removed. The preservative properties of the solution are adequate if, in the conditions of the test, there is a significant fall or no increase, as appropriate, in the number of micro-organisms in the inoculated solution after 14 and 28 days. ATCC stands for the deposit number of the micro-organism at the American Type Culture Collection ATCC.

TABLE 10A

Preservation efficacy on sample GL-C1P, pH 4.0
(sodium methyl paraben)

| Micro-organism | ATCC | Lot | Inoculation Cfu/g | Time zero | Day 14 | Day 27 |
|---|---|---|---|---|---|---|
| Pseudomonas aeruginosa | 9027 | 4846231 | $4.4 \times 10^5$ | $3.9 \times 10^5$ | <10 | <10 |
| Staphylococcus aureus | 6538 | 4852821 | $5.8 \times 10^5$ | $5.1 \times 10^5$ | <10 | <10 |
| Escherichia coli | 8739 | 4835111 | $7.2 \times 10^5$ | $6.6 \times 10^5$ | <10 | <10 |
| Candida albicans | 10231 | 4434841 | $4.2 \times 10^5$ | $3.8 \times 10^5$ | <10 | <10 |
| Aspergillus brasiliensis | 16404 | 3923205 | $3.5 \times 10^5$ | $3.0 \times 10^5$ | $8.8 \times 10^4$ | $1.7 \times 10^4$ |

TABLE 10B

Preservation efficacy on sample GL-C1P, pH 4.5
(sodium methyl paraben)

| Micro-organism | ATCC | Lot | Inoculation Cfu/g | Time zero | Day 14 | Day 27 |
|---|---|---|---|---|---|---|
| Pseudomonas aeruginosa | 9027 | 4846231 | $4.4 \times 10^5$ | $4.1 \times 10^5$ | <10 | <10 |
| Staphylococcus aureus | 6538 | 4852821 | $5.8 \times 10^5$ | $5.5 \times 10^5$ | <10 | <10 |
| Escherichia coli | 8739 | 4835111 | $7.2 \times 10^5$ | $6.6 \times 10^5$ | <10 | <10 |
| Candida albicans | 10231 | 4434841 | $4.2 \times 10^5$ | $3.9 \times 10^5$ | <10 | <10 |
| Aspergillus brasiliensis | 16404 | 3923205 | $3.5 \times 10^5$ | $3.2 \times 10^5$ | $4.4 \times 10^4$ | $2.0 \times 10^3$ |

TABLE 10C

Preservation efficacy on sample GL-H1B, pH 4.0
(benzoic acid)

| Micro-organism | ATCC | Lot | Inoculation Cfu/g | Time zero | Day 14 | Day 27 |
|---|---|---|---|---|---|---|
| Pseudomonas aeruginosa | 9027 | 4846231 | $4.4 \times 10^5$ | $4.0 \times 10^5$ | <10 | <10 |
| Staphylococcus aureus | 6538 | 4852821 | $5.8 \times 10^5$ | $5.3 \times 10^5$ | <10 | <10 |
| Escherichia coli | 8739 | 4835111 | $7.2 \times 10^5$ | $6.6 \times 10^5$ | <10 | <10 |
| Candida albicans | 10231 | 4434841 | $4.2 \times 10^5$ | $3.9 \times 10^5$ | <10 | <10 |
| Aspergillus brasiliensis | 16404 | 3923205 | $3.5 \times 10^5$ | $3.1 \times 10^5$ | $2.3 \times 10^3$ | <10 |

TABLE 10D

Preservation efficacy on sample GL-C1BB, pH 4.0
(sodium benzoate)

| Micro-organism | ATCC | Lot | Inoculation Cfu/g | Time zero | Day 14 | Day 27 |
|---|---|---|---|---|---|---|
| Pseudomonas aeruginosa | 9027 | 4846231 | $4.4 \times 10^5$ | $5.4 \times 10^5$ | <10 | <10 |
| Staphylococcus aureus | 6538 | 4852821 | $5.8 \times 10^5$ | $6.0 \times 10^5$ | <10 | <10 |
| Escherichia coli | 8739 | 4835111 | $7.2 \times 10^5$ | $6.9 \times 10^5$ | <10 | <10 |
| Candida albicans | 10231 | 4434841 | $4.2 \times 10^5$ | $3.1 \times 10^5$ | $4.0 \times 10^1$ | <10 |
| Aspergillus brasiliensis | 16404 | 3923205 | $3.5 \times 10^5$ | $3.7 \times 10^5$ | $3.0 \times 10^3$ | $5.6 \times 10^2$ |

TABLE 10E

Preservation efficacy on sample GL-H1S, pH 4.0
(sorbic acid)

| Micro-organism | ATCC | Lot | Inoculation Cfu/g | Time zero | Day 14 | Day 27 |
|---|---|---|---|---|---|---|
| Pseudomonas aeruginosa | 9027 | 4846231 | $4.4 \times 10^5$ | $4.1 \times 10^5$ | <10 | <10 |
| Staphylococcus aureus | 6538 | 4852821 | $5.8 \times 10^5$ | $5.0 \times 10^5$ | <10 | <10 |
| Escherichia coli | 8739 | 4835111 | $7.2 \times 10^5$ | $6.3 \times 10^5$ | <10 | <10 |
| Candida albicans | 10231 | 4434841 | $4.2 \times 10^5$ | $3.5 \times 10^5$ | <10 | <10 |
| Aspergillus brasiliensis | 16404 | 3923205 | $3.5 \times 10^5$ | $3.0 \times 10^5$ | $7.9 \times 10^3$ | <10 |

From the above preservation efficacy tests, it can be observed that sodium methyl paraben is a less efficient preservative at the pH values of 4.0 and 4.5 as compared to benzoic acid, sodium benzoate or sorbic acid, that all comply with the relevant criteria. It is to be noted that results similar to that of sodium benzoate were obtained when using potassium benzoate as preservative, and results similar to that of sorbic acid when potassium or sodium sorbate were used as preservative. The presence of a buffer did not significantly change the results.

TABLE 10F

Preservation efficacy on solution 1 of U.S. Pat. No. 9,345,722

| Micro-organism | ATCC | Lot | Inoculation Cfu/g | Time zero | Day 14 |
|---|---|---|---|---|---|
| Pseudomonas aeruginosa | 9027 | 4846231 | $5.4 \times 10^5$ | $4.9 \times 10^5$ | <10 |
| Staphylococcus aureus | 6538 | 4852821 | $5.0 \times 10^5$ | $5.0 \times 10^5$ | <10 |
| Escherichia coli | 8739 | 4835111 | $6.9 \times 10^5$ | $6.1 \times 10^5$ | <10 |
| Candida albicans | 10231 | 4434841 | $3.7 \times 10^5$ | $3.7 \times 10^5$ | <10 |
| Aspergillus brasiliensis | 16404 | 3923205 | $3.8 \times 10^5$ | $4.0 \times 10^5$ | $3.1 \times 10^4$ |

It can be observed that for solution 1 of U.S. Pat. No. 7,345,722, the antimicrobial efficacy is suboptimal, and microbial growth after only 14 days is an order of magnitude higher than that of the samples H1S, H1B and C1BB of the invention.

In the above stability and preservation experiments, similar results were obtained when a lower concentration of levothyroxine of 10 μg/ml or 5 μg/ml was used.

The invention claimed is:

1. An oral levothyroxine solution having a pH between 3.5-4.9 and being stable at 40° C. for at least 6 months, comprising:
    i) 0.0002-0.004 w/v % levothyroxine or a salt thereof;
    ii) 20-80 w/w % of a water-miscible organic solvent selected from the group consisting of glycerol, propylene glycol and polyethylene glycol or a sugar alcohol selected from the group consisting of maltitol, maltodextrin and sorbitol or a combination of the water-miscible organic solvents and/or the sugar alcohols;
    iii) 0.03-0.1 w/v % of a preservative selected from the group consisting of benzoic acid, sodium benzoate, potassium benzoate, sorbic acid, sodium sorbate, potassium sorbate, paraben, and a combination thereof; and
    iv) water.

2. The oral Levothyroxine solution of claim 1, wherein the composition comprises levothyroxine or a salt thereof at a concentration of 2-30 μg per ml of the composition.

3. The oral Levothyroxine solution of claim 2, wherein the composition comprises levothyroxine or a salt thereof at a concentration of 25 μg in 5 ml, 50 μg in 5 ml or 100 μg in 5 ml, having a pH of 3.5-4.5.

4. The oral levothyroxine solution of claim 1, wherein the water miscible organic solvent comprises glycerol.

5. The oral levothyroxine solution of claim 1, wherein the preservative comprises sodium benzoate or potassium benzoate.

6. The oral levothyroxine solution of claim 4, comprising: 0.0004-0.004 w/v% levothyroxine or a salt thereof, 60-80 w/v % glycerol and water.

7. A method for the preparation of an oral levothyroxine solution of claim 1, comprising the steps of:
   a) combining:
      i) levothyroxine or a salt thereof;
      ii) a water-miscible organic solvent selected from the group consisting of glycerol, propylene glycol and polyethylene glycol, a sugar alcohol selected from the group consisting of maltitol, maltodextrin and sorbitol or a combination thereof, of the water-miscible organic solvents and/or sugar alcohols;
      iii) a preservative selected from the group consisting of benzoic acid, sodium benzoate, potassium benzoate, sorbic acid, sodium sorbate, potassium sorbate, paraben, and a combination thereof; and
      iv) water;
   b) adjusting the pH to at least 8 providing a basic aqueous medium;
   c) dissolving the levothyroxine in the basic aqueous medium to yield a levothyroxine solution; and d) lowering the pH of the levothyroxine solution to between 3.5-4.9, thereby obtaining the oral levothyroxine solution of claim 1.

8. The method of claim 7, wherein the salt of levothyroxine is sodium salt.

9. The method of claim 7, wherein the water-miscible organic solvent is selected from the group consisting of glycerol, propylene glycol, polyethylene glycol and a combination thereof.

10. The method of claim 7, wherein the pH in step b) is adjusted to between 9 and 11.

11. The method of claim 7, further comprising the step of buffering the composition, the buffer comprising an acidic buffer component and a basic buffer component.

12. The method of claim 11, wherein the buffer is chosen from the group, selected from the group consisting of:
   citric acid-sodium or potassium citrate,
   boric acid-sodium borate,
   hydrochloric acid-potassium hydrogen phthalate,
   adipic acid-sodium adipate,
   acetic acid-sodium acetate,
   potassium hydrogen phthalate-sodium hydroxide,
   malic acid-sodium malate, and
   maleic acid-sodium maleate.

13. The method of claim 7, wherein in step d) the pH is lowered to between 3.5-4.5.

14. The method of claim 7, wherein the preservative comprises sodium benzoate or potassium benzoate.

15. The oral levothyroxine composition of claim 1, wherein the weight ratio between water and the water miscible organic solvent and/or the sugar alcohol is in the range of 1:0.1-20.

16. The method of claim 7, wherein after steps b) and c) the weight ratio between water and water miscible organic solvent or the sugar alcohol is in the range of 1:0.1-20.

17. The oral levothyroxine solution of claim 1, in which the water-miscible organic solvent is present without a sugar alcohol and wherein, after storage for 6 months at 40° C., the levothyroxine content is more than 94%.

18. The oral levothyroxine solution of claim 1, in which the water-miscible organic solvent is present without a sugar alcohol and wherein, after storage for 6 months at 40° C., the levothyroxine content is more than 95%.

* * * * *